United States Patent [19]

Loper

[11] Patent Number: 5,387,266
[45] Date of Patent: Feb. 7, 1995

[54] MANNICH BASE DERIVATIVES, AND THE PRODUCTION AND USES THEREOF

[75] Inventor: John T. Loper, Richmond, Va.

[73] Assignee: Ethyl Corporation, Richmond, Va.

[21] Appl. No.: 76,460

[22] Filed: Jun. 11, 1993

[51] Int. Cl.$^6$ .................. C10L 1/22; C07C 275/00
[52] U.S. Cl. .................... 44/415; 44/417; 564/47
[58] Field of Search .............. 44/415, 417; 564/47

[56] References Cited

U.S. PATENT DOCUMENTS

| | | | |
|---|---|---|---|
| 3,061,641 | 10/1962 | Wright, Jr. et al. | 564/47 |
| 3,413,347 | 11/1968 | Worrel | 260/570.5 |
| 3,725,277 | 4/1973 | Worrel | 252/51.5 R |
| 3,734,965 | 5/1973 | Becker | 260/570.5 P |
| 3,736,357 | 5/1973 | Piasek et al. | 564/47 |
| 3,948,619 | 4/1976 | Worrel | 44/58 |
| 3,985,802 | 10/1976 | Piasek et al. | 564/47 |
| 4,006,089 | 2/1977 | Chibnik | 252/51.5 R |
| 4,083,699 | 4/1978 | Chibnik | 44/75 |
| 4,160,648 | 7/1979 | Lewis et al. | 44/63 |
| 4,197,409 | 4/1980 | Lilburn | 560/158 |
| 4,231,759 | 11/1980 | Udelhofen et al. | 44/75 |
| 4,270,930 | 6/1981 | Campbell | 44/71 |
| 4,310,592 | 1/1982 | Schmitz | 428/288 |
| 4,376,783 | 3/1983 | Anatol et al. | 564/47 |
| 4,383,102 | 5/1983 | McDaniel et al. | 528/107 |
| 4,398,921 | 8/1983 | Rifkin et al. | 44/56 |
| 4,456,454 | 1/1984 | Jenkins, Jr. | 44/73 |
| 4,508,541 | 4/1985 | Kaufman et al. | 44/71 |
| 4,604,103 | 8/1986 | Campbell | 44/72 |
| 4,714,750 | 12/1987 | Grigsby, Jr. et al. | 528/99 |
| 4,747,851 | 5/1988 | Sung et al. | 44/72 |
| 4,787,996 | 11/1988 | Horodysky et al. | 252/51.5 R |
| 4,810,354 | 3/1989 | Roling et al. | 208/48 AA |
| 4,847,415 | 7/1989 | Roling et al. | 564/367 |
| 4,927,912 | 5/1990 | Speranza et al. | 528/405 |
| 4,944,770 | 7/1990 | Sung | 44/415 |
| 5,021,429 | 6/1991 | Martin-Smith | 564/47 |
| 5,039,310 | 8/1991 | Blain et al. | 44/424 |
| 5,098,986 | 3/1992 | Speranza et al. | 528/162 |
| 5,286,266 | 2/1994 | Herbstman | 44/417 |

FOREIGN PATENT DOCUMENTS 1085857 10/1967 United Kingdom .
2049716 12/1980 United Kingdom .

Primary Examiner—Ellen M. McAvoy
Attorney, Agent, or Firm—John F. Sieberth

[57] ABSTRACT

Compounds are described in which a phenolic moiety is linked by a Mannich base linkage to an alkylene-poly(oxyalkylene) moiety, and a polyamine moiety is linked to the alkylene-poly(oxyalkylene) moiety by a urea linkage involving one of the nitrogen atoms of the polyamine moiety. These compounds are highly effective detergent/dispersants for use in fuels and other media.

30 Claims, No Drawings

MANNICH BASE DERIVATIVES, AND THE PRODUCTION AND USES THEREOF

TECHNICAL FIELD

This invention relates to novel and eminently useful Mannich base derivatives. More particularly, it relates to novel condensation products having detergent and dispersant properties, and to fuels and lubricants containing such products.

BACKGROUND

Over the years a considerable amount of effort has been devoted to the discovery and development of chemical products having detergent and/or dispersant properties when used in hydrocarbonaceous fuels and/or natural and synthetic oils of lubricating viscosity. Fuel-soluble detergents are used in order to control the amount and character of deposits which tend to form in the fuel induction system of internal combustion engines. Oil-soluble detergent-dispersants are widely used in lubricating oils to control deposit and varnish formation, and to keep sludge and other solid matter is suspension in the oil. A small sampling of efforts along these lines is reflected in U.S. Pat. Nos. 3,413,347; 3,725,277; 3,948,619; 4,006,089; 4,083,699; 4,160,648; 4,197,409; 4,231,759; 4,398,921; 4,508,541; 4,604,103; 4,747,851; 4,787,996; 4,944,770; and 5,039,310.

The concomitant advent of Government regulations on engine emissions, the development of engines that operate at higher temperatures and with more sophisticated fuel induction systems, and the increasing use of new fuel blending components such as alcohols and ethers, has engendered the search for new, highly effective detergent-dispersant additives for use in fuels and lubricants.

THE INVENTION

This invention is based on the discovery that highly effective detergent-dispersants can be formed by suitably linking together appropriate molecular segments in an appropriate sequence by means of appropriate linkages. Furthermore, the resultant condensation products, while complicated from a structural point of view, can be readily prepared in high yield by relatively simple processing using readily available starting materials.

In brief, the products of this invention contain at least three distinct and highly important segments, namely a phenolic moiety, an alkylene-poly(oxyalkylene) moiety and a polyamine moiety. The phenolic moiety is linked to the alkylene-poly(oxyalkylene) moiety by means of a Mannich base linkage, and the alkylene-poly(oxyalkylene) moiety in turn is linked to the polyamine moiety by means of a urea linkage involving one of the nitrogen atoms of the polyamine moiety.

In one of its forms, this invention involves the provision of a compound of the formula:

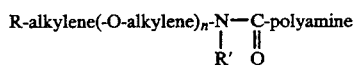  (1)

where R is a hydroxybenzylamino group; the "alkylene" groups can be the same or different and contain from 2 to 20 carbon atoms each; n represents the average number of oxyalkylene groups in the molecule; R' is a hydrogen atom or a hydrocarbyl group, preferably a hydrogen atom; and the polyamine group has 2 to 10 nitrogen atoms, and is bonded to the carbonyl group by means of one of the nitrogen atoms of the polyamine group.

The compounds of Formula (1) above where R' is a hydrogen atom can be formed in a two-step process. The first step involves preparing a Mannich base by a Mannich condensation reaction among substantially equimolar quantities of a phenolic compound, an aldehyde such as formaldehyde, acetaldehyde, propionaldehyde, furfuryl aldehyde, etc. (preferably formaldehyde or a formaldehyde-producing reagent such as paraformaldehyde), and a suitable polyoxyalkylene diamine. In the second step the Mannich base so formed is reacted with a dialkyl carbonate or phosgene followed by reaction with a polyamine whereby the desired product is formed via bonding of the polyamine group by one of its nitrogen atoms to the carbonyl group of the urea linkage so formed. To form the compounds of Formula (1) where R' is a hydrocarbyl group, the Mannich base from the first step is converted into a Schiff base by reaction with an aldehyde, and the Schiff base is reduced by catalytic hydrogenation, or by use of a reducing agent such as LiAlH$_4$, NaH, or B$_2$H$_6$, to form the corresponding secondary amine, R-alkylene(—O-alkylene)$_n$—NHR', which is then reacted with a dialkyl carbonate or phosgene followed by reaction with a polyamine.

Accordingly, another embodiment is a process for the preparation of a compound of Formula (1) wherein R' is a hydrogen atom which comprises:

(a) reacting a phenolic compound with an aldehyde (preferably formaldehyde or a formaldehyde-producing reagent) and a compound of the formula H$_2$N-alkylene(—O-alkylene)$_n$—NH$_2$ to form a product of the formula R-alkylene(—O-alkylene)$_n$—NH$_2$; and b) reacting the product formed in a) with a dialkylcarbonate or phosgene and thereafter with a polyamine having 2 to 10 nitrogen atoms per molecule; wherein R, "alkylene" and n are as described above.

The process of this invention for the preparation of a compound of Formula (1) wherein R' is a hydrocarbyl group comprises:

a) reacting a phenolic compound with an aldehyde, (preferably formaldehyde or a formaldehyde-producing reagent) and a compound of the formula H$_2$N-alkylene(—O-alkylene)$_n$—NH$_2$ to form a product of the formula R-alkylene(—O-alkylene)$_n$—NH$_2$;

b) reacting the product formed in a) with an aldehyde to convert said product to a Schiff base;

c) reducing the Schiff base to convert the Schiff base into the corresponding secondary amine; and d) reacting the secondary amine formed in d) with a dialkylcarbonate or phosgene and thereafter with a polyamine having 2 to 10 nitrogen atoms per molecule; wherein R, "alkylene" and n are as described above.

Preferred compounds of this invention can be depicted by the formula:

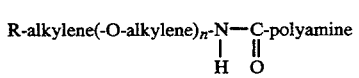  (2)

where R is a 3,5-dihydrocarbyl-4-hydroxybenzylamino group or a 3,5-dihydrocarbyl-2-hydroxybenzylamino group or a 5-hydrocarbyl-2-hydroxybenzylamino group; the "alkylene" groups can be the same or different and contain from 2 to 20 carbon atoms each; n represents the average number of oxyalkylene groups in the molecule; and the polyamine group has 2 to 10 nitrogen atoms, and is bonded to the carbonyl group by means of one of the nitrogen atoms of the polyamine group.

In formulas (1) and (2) above, n is an average number in the range of 2 to about 150, preferably in the range of 2 to about 100, more preferably in the range of about 5 to about 90, and most preferably in the range of about 10 to about 80.

The compounds of Formula (2) above can be produced by the same two-step process as described above with the proviso that the phenolic compound used in step a) is (i) a 2,6-dihydrocarbyl phenol, (ii) a 2,4-dihydrocarbyl phenol, (iii) a 4-hydrocarbyl phenol, or (iv) a mixture of any two or all three of (i), (ii) and (iii).

Two additional embodiments of this invention comprise respectively, compounds of the formula:

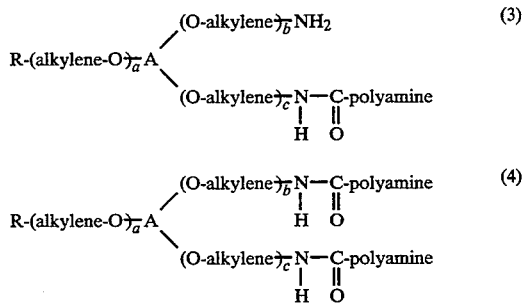

where R is a hydroxybenzylamino group, "alkylene" and "polyamine" are as described above, A is the hydrocarbyl group of a triol, and a, b and c represent the number of oxyalkylene groups present in the respective oxyalkylene moieties, typically in the range of 1 to about 35 with the total of a, b and c being in the range of about 5 to about 100. Thus this invention provides, inter alia, compounds of Formula (3), compounds of Formula (4) and mixtures of compounds of Formulas (3) and (4). These compounds are formed by conducting a Mannich condensation reaction among a phenolic compound, an aldehyde and an oxyalkylene triamine of the type formed by reacting an alkylene oxide with triol initiator (e.g., trimethylol propane, glycerine, etc.) and aminating the terminal hydroxyl groups. Then in a second step, the Mannich base so formed is reacted with a dialkyl carbonate or phosgene and thereafter with a polyamine. To produce the compounds of Formula (3), the Mannich base, the dialkyl carbonate or phosgene, and the polyamine are employed in approximately equimolar proportions. The compounds of Formula (4) are formed by reacting two mols of the dialkyl carbonate or phosgene and two mols of the polyamine, per mol of the Mannich base.

It will be understood from the foregoing that in the compounds of this invention, the Mannich base linkage which bonds the phenolic moiety to the alkylene-poly(oxyalkylene) moiety has the structure:

—CHR*—NH— where R* is a hydrogen atom or a hydrocarbyl group, preferably a hydrogen atom. The —CHR*— portion of this linkage is derived from the aldehyde, and the —NH— portion of this linkage is derived from one of the primary amino groups of the polyoxyalkylene diamine or triamine used in the first step of the above reaction sequences. The urea linkage in the compounds of this invention typically has the structure:

—NR'—CO—NH where R' is a hydrogen atom or a hydrocarbyl group, preferably a hydrogen atom. The —NR'— portion of this linkage is derived from an amino group of the Mannich base formed in the first step of the above reaction sequences, and the R' is a hydrocarbyl group when the Mannich base has been converted to a Schiff base and reduced, but otherwise is a hydrogen atom. The —CO— portion of this linkage is derived from the dialkyl carbonate or phosgene reactant, and the —NH— portion of this linkage is derived from a primary amino group in the polyamine reactant used in the final step of the above reaction sequences.

In the compounds of Formulas (1), (3) and (4) above, the hydroxybenzylamino group, R, is preferably substituted on the ring by one or more hydrocarbyl groups—e.g., aliphatic or cycloaliphatic groups—each of which is free of acetylenic unsaturation. The ring can thus be substituted, for example, by up to four acyclic hydrocarbyl substituents, although usually the ring will have less than four such substituents, and typically will have from 1 to 2 acyclic hydrocarbyl substituents. Preferably, the "alkylene" groups of the compounds of this invention each contain 2 to 10, more preferably 2 to 5 and still more preferably 3 to 4 carbon atoms, and the "polyamine" group of the compounds of this invention preferably contains at least one primary amino group per molecule (and thus is formed from a polyamine having at least two primary amino groups per molecule).

The above and other embodiments of this invention will be still further apparent from the ensuing description and appended claims.

As noted above, the compounds of this invention have a phenolic moiety linked to an alkylene-poly(oxyalkylene) moiety by means of a Mannich base linkage, and the alkylene-poly(oxyalkylene) moiety in turn is linked to a polyamine moiety by means of a urea linkage involving one of the nitrogen atoms of the polyamine moiety. To form the phenolic moiety and the Mannich base linkage, three types of reactants are employed, namely, a monohydric phenolic compound, an aldehyde, and an alkylene-poly(oxyalkylene) polyamine having at least one primary amino group, and preferably two or three primary amino groups.

Phenolic Compounds

While the phenolic compound can be phenol itself, preferably it is substituted on the ring by from 1 to 4, more preferably by from 1 to 3, and still more preferably by from 1 to 2 hydrocarbyl groups. Such hydrocarbyl groups can range from lower alkyl or alkenyl groups (viz., alkyl groups of 1 to about 6 carbon atoms or alkenyl groups of 2 to about 6 carbon atoms) up to long chain hydrocarbyl groups having 300 or more carbon atoms such as alkyl or alkenyl groups derived from polypropenes, polybutenes, polyisobutenes, polyamylenes, copolymers of ethylene and propylene, copolymers of ethylene and butene, copolymers of ethylene and isobutene, copolymers of propene and isobutene, copolymers of propene, butene and isobutene, and the like, having number average molecular weights of up to about 3000 or more. The hydrocarbyl group(s) can also be cycloalkyl or cycloalkenyl groups, aryl groups, aralkyl groups, polyunsaturated aliphatic hydrocarbyl groups, or the like. The number of hydrocarbyl groups present on the phenolic ring (which cannot exceed four) will to some extent be dependent upon steric factors such as the size and structure of the hydrocarbyl group. When substituted, the phenolic compound will usually have one or two hydrocarbyl groups. In many cases the longer chain hydrocarbyl group(s) will be bonded to the phenolic ring by a secondary or tertiary carbon atom. On the other hand, the short chain hydrocarbyl group(s) will be bonded to the phenolic ring by primary, secondary or tertiary carbon atoms. Typically, the phenolic compound used will have its para position and/or at least one ortho position unsubstituted (except by a hydrogen atom), and at least one such position will be sufficiently unhindered as to be capable of undergoing the Mannich reaction with the aldehyde and alkylenepoly(oxyalkylene) polyamine.

Thus the phenolic moiety can be derived from such phenols as o- and/or p-tert-amylphenol; o-benzylphenol; p-benzylphenol; p-secbutylphenol; o-tert-butylphenol; p-tert-butylphenol; o-cyclohexylphenol; o-cyclohexenylphenol; p-octylphenol (where the octyl group is derived from isobutene dimer); p-nonylphenol (where the nonyl group is derived from propene trimer); p-dodecylphenol (where the dodecyl group is derived from isobutene trimer); monoalkylated phenols derived from oligomers or polymers of propene having from 4 up to about 100 propene units per molecule; monoalkylated phenols derived from oligomers or polymers of isobutene, having from 4 up to about 100 isobutene units per molecule; monoalkylated o-, m-, and/or p-cresol wherein the alkyl group is derived from propene dimer, propene trimer, and/or higher oligomers or polymers of propene; monoalkylated o-, m-, and/or p-cresol wherein the alkyl group is derived from isobutene dimer, isobutene trimer, and/or higher oligomers or polymers of isobutene; monoalkylated o-cyclohexylphenol wherein the alkyl group on the phenolic ring is derived from propene dimer, propene trimer, and/or higher oligomers or polymers of propene; monoalkylated o-cyclohexylphenol wherein the alkyl group on the phenolic ring is derived from isobutene dimer, isobutene trimer, and/or higher oligomers or polymers of isobutene; monoalkylated p-benzylphenol wherein the alkyl group on the phenolic ring is derived from propene dimer, propene trimer, and/or higher oligomers or polymers of propene; monoalkylated p-benzylphenol wherein the alkyl group on the phenolic ring is derived from isobutene dimer, isobutene trimer, and/or higher oligomers or polymers of isobutene; o-, m- and/or p-phenylphenol wherein the alkyl group on the phenolic ring is derived from propene dimer, propene trimer, and/or higher oligomers or polymers of propene; monoalkylated p-phenylphenol wherein the alkyl group on the phenolic ring is derived from isobutene dimer, isobutene trimer, and/or higher oligomers or polymers of isobutene; o-, m-, and/or p-styrylphenol wherein the alkyl group on the phenolic ring is derived from propene dimer, propene trimer, and/or higher oligomers or polymers of propene; monoalkylated p-styrenated phenol wherein the alkyl group on the phenolic ring is derived from isobutene dimer, isobutene trimer, and/or higher oligomers or polymers of isobutene; o-, m-, and/or p-cyclopentenylphenol wherein the alkyl group on the phenolic ring is derived from propene dimer, propene trimer, and/or higher oligomers or polymers of propene; monoalkylated p-cyclopentenylphenol wherein the alkyl group on the phenolic ring is derived from isobutene dimer, isobutene trimer, and/or higher oligomers or polymers of isobutene; and the like.

Suitable trihydrocarbyl phenols and tetrahydrocarbyl phenols are exemplified by 2,3,4-trimethylphenol; 2,3,5-trimethylphenol; 2,3,5-trimethylphenol; 2,3,4-triethylphenol; 2,3,5-triethylphenol; 2,3,5-triethylphenol; 6-tert-butyl-2,3-dimethyl phenol; 2,3- and/or 2,5-xylenol alkylated in the 4- or 6-position by an alkyl group derived from propene dimer, propene trimer, and/or higher oligomers or polymers of propene; 2,3- and/or 2,5-xylenol alkylated in the 4- or 6-position by an alkyl group derived from isobutene dimer, isobutene trimer, and/or higher oligomers or polymers of isobutene; 2,3,5-trimethylphenol alkylated in the 4- or 6-position by an alkyl group derived from propene dimer, propene trimer, and/or higher oligomers or polymers of propene; 2,3,5-trimethylphenol alkylated in the 4- or 6-position by an alkyl group derived from an oligomer or polymer of ethylene and propene or of ethylene and isobutene; 2,3,4,5-tetramethylphenol; 2,3,5,6-tetramethylphenol; 2,6-diethyl-3,5-dimethylphenol; and the like.

Preferred dialkylphenols for use in preparing the compounds of this invention include 2-methyl-6-tert-butylphenol, 2,6-diisopropylphenol, 2,6-di-tert-butylphenol, 2-methyl-4-tert-butylphenol, 2-tert-butyl-4-methylphenol, 2,4-diisopropylphenol, 2,4-di-tert-butylphenol, 2-methyl-6-tert-amylphenol, 2-methyl-4-tert-amylphenol, 2-ethyl-6-tert-butylphenol, 2-tert-butyl-4-ethylphenol, and like compounds wherein the two alkyl groups contain a total of up to about 30 carbon atoms.

Aldehydes

Aldehydes useful in the Mannich reaction for forming the Mannich base intermediates are typified by acetaldehyde, propionaldehyde, butyraldehyde, furfuryl aidehyde, cinnamaldehyde, decyl aldehyde, citral, crotonaldehyde, acrolein, glyoxal, heptaldehyde, methacrolein, tetradecyl aldehyde, and the like. The preferred aldehydes are formaldehyde and formaldehyde-producing reagents such as paraformaldehyde and formalin.

Alkylene-poly(oxyalkylene) Polyamines

Alkylene-poly(oxyalkylene) polyamines having at least two primary amino groups in the molecule suitable for use in forming the Mannich intermediate are amine-terminated compounds having an average of at least two polyoxyalkylene groups per molecule. Generally speaking these compounds have average molecular weights in the range of about 200 to about 10,000, and preferably in the range of about 200 to about 6000. The alkylene groups in these compounds can be the same or different and generally will each contain from 2 to 20, preferably from 2 to 10, more preferably from 2 to 5 and still more preferably from 3 to 4 carbon atoms. When different alkylene groups are present, these can be randomly disposed within the poly(oxyalkylene) chain or they can be arranged in blocks within the chain, such as for example one or more oxyethylene groups followed by a block of oxypropylene groups, or one or more oxyethylene groups followed by a block of oxybutylene groups followed by one or more oxyethylene groups, etc. Usually the alkylene groups will have the configuration:

$$-CHR''-CH_2-$$

where R″ is a hydrogen atom or a $C_1$–$C_{18}$ alkyl group, preferably a hydrogen atom or a $C_1$–$C_8$ alkyl group, more preferably a hydrogen atom or a $C_1$–$C_3$ alkyl group, and still more preferably a $C_1$–$C_2$ alkyl group. Compounds in which at least 90% of the oxyalkylene groups are oxypropylene (R″ is methyl) or oxybutylene (R″ is ethyl) or a combination of oxypropylene and oxybutylene groups are particularly preferred.

Various types of amine-terminated alkylene-poly(oxyalkylene) compounds can be used in forming the intermediates of the compounds of this invention. For example, one category of such amine-terminated alkylene-poly(oxyalkylene) compounds can be represented by the formula:

$$H_2N\text{-alkylene-(O-alkylene)}_x\text{-NH}_2 \quad (5)$$

where "alkylene" is as defined above and x is in the range of from 2 to 150.

Another category of amine-terminated alkylene-poly(oxyalkylene) compounds is comprised of urea condensates of some of lower molecular weight compounds of formula (5) above. Accordingly this category can be represented by the formula:

$$H_2N\text{-alkylene-(O-alkylene)}_y\text{-NH-CO-NH-(alkylene)}_z\text{-alkylene-NH}_2 \quad (6)$$

where "alkylene" is as defined above, and y and z can be the same or different and each is in the range of from 2 to 20.

Still another category of amine-terminated alkylene-poly(oxyalkylene) compounds is made up of compounds having three primary amino groups in the molecule formed by reaction of an alkylene oxide with a triol initiator followed by amination of the terminal hydroxyl groups. Such compounds can be represented by the formula:

(7)

where A is the hydrocarbyl residue of a triol initiator such as trimethylol propane, trimethylol butane, triethylol propane, glycerine, etc., "alkylene" is as defined above, and a, b and c can be the same or different and each is in the range of from 1 to about 35. Typically, the sum of a, b and c is in the range of about 5 to about 100.

Methods for the preparation of the amine-terminated alkylenepoly(oxyalkylene) compounds are known and reported in the literature. Indeed a number of such compounds are available as articles of commerce. By way of example, use can be made of products available from Texaco Chemical Company under the Jeffamine trademark, such as Jeffamine ® D-230, D-400, D-2000, D-4000, DU-700, ED-600, ED-900, ED-2001, ED-4000, ED-6000, T-403, T-3000, T-5000, DB-2001, and equivalent products. The Jeffamine ® diamine D-series have the structure:

$$H_2NCHR''CH_2\text{-(OCH}_2CHR''\text{)}_x\text{-NH}_2 \quad (8)$$

where each R″ is a methyl group. The individual products of this type are as indicated in the Table I.

TABLE I

| Product Designation | Value of x | Approximate Molecular Weight |
|---|---|---|
| D-230 | 2–3 | 230 |
| D-400 | 5–6 | 400 |
| D-2000 | 33 (Avg.) | 2,000 |
| D-4000 | 68 (Avg.) | 4,000 |

Jeffamine DB-2001 has the structure of Formula (8) above except that each R″ is ethyl and the product has an approximate molecular weight of 2,000.

The Jeffamine ED-series of polyether diamines are depicted by the formula:

$$H_2NCHCH_2\text{-(OCHCH}_2\text{)}_a\text{-(OCH}_2CH_2\text{)}_b\text{-(OCH}_2CH\text{)}_c\text{-NH}_2 \quad (9)$$
$$\quad\;\; | \qquad\qquad | \qquad\qquad\qquad\qquad\qquad | $$
$$\;\;\, CH_3 \qquad\quad CH_3 \qquad\qquad\qquad\qquad\;\; CH_3$$

Individual products of this type are identified in the Table II.

TABLE II

| Product Designation | Approximate Value of b | Approximate Value of a + c | Approximate Molecular Weight |
|---|---|---|---|
| ED-600 | 8.5 | 2.5 | 600 |
| ED-900 | 15.5 | 2.5 | 900 |
| ED-2001 | 40.5 | 2.5 | 2,000 |
| ED-4000 | 86.0 | 2.5 | 4,000 |

Jeffamine DU-700 has the structure of Formula (6) above wherein each "alkylene" is an isopropylene group, and each of y and z is from 5 to 6.

The individual products of the T-series of Jeffamine ® triamines have the structure of Formula (7) above in which each "alkylene" is an isopropylene group, and A is the hydrocarbyl residue of the triol initiator identified in the Table III.

TABLE III

| Product Designation | Triol Initiator | Approximate Molecular Wt. | Mols of Propylene oxide |
|---|---|---|---|
| T-403 | Trimethylolpropane | 440 | 5–6 |
| T-3000 | Glycerine | 3,000 | 50 |
| T-5000 | Glycerine | 5,000 | 85 |

The reaction conditions used in the Mannich reaction involve temperatures in the range of from about 65° to about 160° C. The reactants are preferably employed in approximately equimolar quantities. The reaction can be conducted either in bulk (i.e., without a solvent) or in a suitable inert liquid diluent or solvent such as toluene, xylene, petroleum ethers, ligroin, etc. In either case, water evolved in the reaction is preferably removed from the reaction system. When conducting the process in bulk, reaction times of up to about 12 hours are typical. On the other hand, when conducting the process in a solvent, shorter reaction times can be employed. For example, when conducting the reaction in a diluent and removing the water via azeotropic distillation, reaction times in the range of from 0.5 to 2 hours can be used.

When converting the intermediate to a Schiff base, the intermediate formed as above is reacted with a suitable aldehyde such as those described above. This reaction is typically conducted in the presence of an inert solvent such as described above at a temperature in the range of about 65° to about 160° C. The Schiff base is then reduced by use of catalytic hydrogenation or by use of a suitable reducing agent such as lithium aluminum hydride, sodium aluminum hydride, diborane, diethylaluminum hydride, diisobutylaluminum hydride, sodium hydride, potassium hydride, or the like. This reduction converts the Schiff base into the corresponding secondary amine.

The Mannich base (or the secondary amine derivative thereof) is then reacted with a dialkyl carbonate or phosgene followed by reaction with a polyamine having at least one primary amino group, and preferably two or more primary amino groups, in order to form a urea linkage involving an amino group of the Mannich base (or the secondary amine derivative thereof) and an amino group of the polyamine. Typically this linkage has the structure:

—NR'—CO—NH— where R' is as defined above. The reaction with the dialkyl carbonate is typically conducted at a temperature in the range of about 60° to about 140° C. On the other hand, when using phosgene, lower temperatures will generally be used such as temperatures in the range of about 30° to about 45° C. The reaction of the carbamate with the polyamine to form the urea linkage is usually conducted at a temperature in the range of about 60° to about 140° C., although other temperatures can be used.

Polyamines

The polyamines can be and preferably are hydrocarbyl amines although they can contain one or more suitable substituents such as ether oxygen atoms (—O—), hydroxyl groups (—OH), thioether sulfur atoms (—S$_n$—), mercapto groups (—SH), halogen atoms (—X), keto groups (>CO), thioketo groups (>CS), carboxyl groups (—COOH), ester groups (—COOR), nitrilo groups (—CN), thiocyano groups (—SCN), nitro groups (—NO$_2$), hetero nitrogen atoms (—N=), and the like, provided that each substituted hydrocarbyl group of the amine retains its predominantly hydrocarbonaceous character. When substituted polyamines are used, they preferably have one or more ether oxygen linkages, one or more thioether linkages, one or more hetero nitrogen atoms and/or one or more hydroxyl groups.

Illustrative polyamines which may be employed in forming the compounds of this invention include such compounds as tetraaminoneopentane; 1-(β-aminoethyl)-2-imidazolidone, N,N'-di(β-aminoethyl)imidazolidone-2; 2-(2-aminoethylamino)-5-nitropyridine; 3-amino-N-ethylpiperidine; 2-(2-aminoethyl)-pyridine;5-aminoindole;3-amino-5-mercapto-1,2,4-triazole; N-aminoethylpiperazine; N,N'-bis(aminoethyl)piperazine; 4-(aminomethyl)-piperidine; ethylenediamine; 1,2-propylenediamine; 1,3-propylene diamine; methylaminopropylenediamine; dipropylenetriamine; di-(1,2-butylene)triamine; N-(2-aminoethyl)-1,3-propanediamine; hexamethylenediamine; N-(β-cyanoethyl)ethane-1,2-diamine; 1,3,6,9-tetraaminooctadecane; 1,3,6-triamino-9-oxadecane; N-methyl-1,2-propanediamine; tetra-(1,2-propylene)pentamine; diethylenetriamine; triethylenetetramine; tetraethylenepentamine; pentaethylene-hexamine; adenine; cytosine; guanidine; aminoguanidine; guanylurea; N-(2-aminoethyl)-piperidine; N-(2-aminoethyl)-pyrrolidine; 1,7-diaminoheptane; 1,8-diaminooctane; 1,10-diaminodecane; 1,12-diaminododecane; 3,3-diaminodipropylamine; p-phenylenediamine; N,N'-diaminoguanidine; 1,3-diamino-N-(β-hydroxyethyl)propane; 4,5-diamino-6-hydroxy-2-mercaptopyrimidine; 1,3-diamino-2-propanol; 2,4-diamino-6-hydroxypyrimidine; 1,8-diamino-p-methane; 4,6-diamino-2-mercaptopyrimidine; 1,4-diaminopiperazine; 2,6-diaminopyridine; 3,4-diaminopyridine; 3,5-diamino-1,2,4-triazole; 2,4,6-triaminopyrimidine;triaminoguanidine;amine-terminated polyalkylene glycols (e.g., Jeffamine ® D-230, D-400, D-2000, D-4000 and DB-2001 diamines); urea condensates of amine-terminated polyalkylene glycols (e.g., Jeffamine ® DU-700 urea condensate); amine-terminated polyether diamines (e.g., Jeffamine ® EU-600, ED-900, ED-2001, ED-4000, ED-6000, and EDR-148 diamines); alkylene oxide-based triamines (e.g., Jeffamine ® T-403, T-3000, T-5000 triamines); and the like.

It should be apparent from these illustrative compounds that the polyamines can be aliphatic, cycloaliphatic, aromatic, heterocyclic, aliphatic and cycloaliphatic, aliphatic and aromatic, aliphatic and heterocyclic, cycloaliphatic and aromatic, cycloaliphatic and heterocyclic, aromatic and heterocyclic, etc., in structure; that they may be saturated or contain olefinic, acetylenic and/or aromatic unsaturation; and that they may or may not contain other functional substituents, as long as the compound contains at least one primary amino group capable of forming a urea linkage. Mixtures of suitable polyamines can be used, such as for example, commercial mixtures of straight chain, branched chain and cyclic ethylene polyamines having approximate overall compositions falling in the range corresponding to diethylene triamine to pentaethylene hexamine. The compounds of this invention can be formed from polyamines having combinations of primary and secondary and/or tertiary amino groups in the molecule. In general, compounds formed from polyamines having at least two primary amino groups, especially aliphatic polyamines, are preferred.

Also suitable are high molecular weight hydrocarbyl polyamines typically formed by reacting aliphatic or alicyclic polyhalides (or mixture thereof) containing an average of at least about 40 carbon atoms with one or more amines, such as polyalkylene polyamines. Examples of such hydrocarbyl polyamines and the preparation thereof are described in U.S. Pat. Nos. 3,275,554; 3,438,757; 3,454,555; 3,565,804; 3,671,511; 3,821,302; 3,394,576; and in European Patent Publication No. 382,405, all disclosures of which are incorporated herein by reference. In general, the hydrocarbyl groups of these hydrocarbyl polyamines typically have a number average molecular weight in the range of about 500–10,000, more usually in the range of about 750–5,000, and often in the range of 1000–2500 and normally are of branched-chain structure, having 0–2 sites of unsaturation. The hydrocarbyl groups are typically derived from petroleum mineral oil, or polyolefins, either homopolymers or higher-order polymers, typically formed from 1-olefins of from 2–6 carbon atoms such as ethylene, propylene, isobutylene, 1-butene, amylenes, etc., or combinations thereof.

The following examples illustrate the manner by which various products of this invention can be prepared. These examples are not intended to limit, do not limit, and should not be interpreted as limiting the practice of the generic aspects of this invention.

EXAMPLE 1

Preparation of Mannich Base Intermediate

To a reaction flask equipped with a stirrer, a Dean-Stark trap, and a heating mantle, are charged 309 grams (0.15 mol) of 2,6-di-tert-butylphenol, 4.5 grams (0.15 mol) of paraformaldehyde, 300 grams (0.15 mol) of a polyoxyalkylene diamine having an average molecular weight of about 2000 (Jeffamine D-2000 amine; Texaco Chemical Company), and 310 grams of xylene. While stirring, the mixture is heated to reflux and water evolved during the reaction is collected in the Dean-Stark trap. When the approximate theoretical quantity of water has been collected (about 2.7 mL), a vacuum is applied to the system, and the reaction mixture is concentrated by distilling off xylene diluent and traces of residual water, if any. During the reaction the initially colorless solution typically undergoes several color changes.

EXAMPLE 2

Conversion of Mannich Base to a Diethylene Triamine Derivative

Into a reaction vessel are charged 155.3 grams (0.07 mol) of a Mannich base product formed as in Example 1, 6.3 grams (0.07 mol) of dimethyl carbonate, 250 grams of xylene and 5 grams of Amberlyst ® 15 resin (a highly acidic ion exchange resin available from Rohm & Haas). The mixture is heated at 90° C. until the reaction is complete. Thereupon 7.2 grams (0.07 mol) of diethylene triamine is charged to the reaction mixture which is then refluxed for 3 hours. The product is cooled, filtered and concentrated by distillation at reduced pressure. Typically the product is formed in almost quantitative yields.

EXAMPLE 3

Conversion of Mannich Base to a Triethylene Tetramine Derivative

The procedure of Example 2 is repeated except that the following quantities of materials are used: 155.3 grams (0.07 mol) of a Mannich base product formed as in Example 1, 6.3 grams (0.07 mol) of dimethyl carbonate, 300 grams of xylene, 8 grams of Amberlyst ® 15 resin, and 10.2 grams (0.07 mol) of triethylene tetramine. Yields of desired product typically fall in the range of 90 to 95%.

EXAMPLE 4

Conversion of Mannich Base to a Tetraethylene Pentamine Derivative

The procedure of Example 2 is repeated except that the triethylene tetramine is replaced by 0.07 mol of tetraethylene pentamine.

EXAMPLE 5

Conversion of Mannich Base to a Pentaethylene Hexamine Derivative

The procedure of Example 4 is repeated using 0.07 mol of pentaethylene hexamine instead of the tetraethylene pentamine.

EXAMPLE 6

Conversion of Mannich Base to a Hexamethylene Diamine Derivative

Replacement of the pentaethylene diamine of Example 5 with 0.07 mol of hexamethylene diamine yields a hexamethylene diamine derivative of this invention.

EXAMPLE 7

Conversion of Mannich Base to a 2-(2-Aminoethylamino)-Ethanol Derivative

Use in the procedure of Example 6 of 0.07 mol of 2-(2-aminoethylamino)-ethanol in lieu of the hexamethylene diamine yields a 2-(2-aminoethylamino)-ethanol derivative of this invention.

EXAMPLE 8

Preparation of Mannich Base Intermediate

To a reaction flask equipped with a stirrer, a Dean-Stark trap, and a heating mantle, are charged 65.6 grams (0.25 mol) of p-dodecylphenol in which the dodecyl group was derived from tetramer of propylene, 7.5 grams (0.25 mol) of paraformaldehyde, 500 grams (0.25 mol) of a polyoxyalkylene diamine having an average molecular weight of about 2000 (Jeffamine D-2000 amine; Texaco Chemical Company), and 400 grams of xylene. While stirring, the mixture is heated to reflux and water evolved during the reaction is collected in the Dean-Stark trap. When the approximate theoretical quantity of water has been collected (about 4.5 mL), a vacuum is applied to the system, and the reaction mixture is concentrated by distilling off xylene diluent and traces of residual water, if any.

EXAMPLE 9

Conversion of Mannich Base to a Triethylene Tetramine Derivative

Into a reaction vessel are charged 159.2 grams (0.07 mol) of a Mannich base product formed as in Example 8, 6.3 grams (0.07 mol) of dimethyl carbonate, and 250 grams of xylene. The mixture is heated at 90° C. for approximately 4 hours. After cooling, 10.2 grams (0.07 mol) of triethylene tetramine is charged to the reaction mixture which is then refluxed for 3.5 hours. The product is cooled, filtered and concentrated by distillation at reduced pressure.

The process of this invention can be conducted as a one-pot reaction, as is illustrated in Examples 10-12.

EXAMPLE 10

Preparation of Mannich Base Intermediate and Conversion Thereof to a Triethylene Tetramine Derivative To a reaction flask equipped with a stirrer, a Dean-Stark trap, and a heating mantle, are charged 82.4 grams (0.4 mol) of 2,6-di-tert-butylphenol, 12 grams ( 0.4 mol ) of paraformaldehyde, 800 grams (0.4 tool) of a polyoxyalkylene diamine having an average molecular weight of about 2000 (Jeffamine D-2000 amine; Texaco Chemical Company), and 500 grams of xylene. While stirring, the mixture is heated to reflux and water evolved during the reaction is collected in the Dean-Stark trap. After approximately 7.2 mL of water has been collected, the reaction mixture is cooled and dimethyl carbonate (36 grams; 0.4 mol) is charged thereto. The mixture is heated at 90° C. for 30 minutes and then at 110° C. for another 30 minutes. Triethylene tetramine (58.4 grams; 0.4 mol) is then added to the reaction mixture and the mixture is stirred and heated at reflux for 3 hours. The product is concentrated by distilling off xylene diluent and traces of residual water, if any.

EXAMPLE 11

Preparation of Mannich Base Intermediate and Conversion Thereof to a Triethylene Tetramine Derivative The procedure of Example 10 is repeated except that the following quantities of the following materials are used in the first stage reaction: 51.5 grams (0.25 mol) of 2,6-di-tert-butylphenol, 7.5 grams (0.25 mol) of paraformaldehyde, 100 grams (0.25 mol) of a polyoxyalkylene diamine having an average molecular weight of about 400 (Jeffamine D-400 amine; Texaco Chemical Company), and 800 grams of xylene. After collecting approximately 4.9 grams of water, the second stage is conducted in the same reaction vessel using 22.5 grams (0.25 mol) of dimethyl carbonate, and 36.5 grams (0.25 mol) of triethylene tetramine.

EXAMPLE 12

Preparation of Mannich Base Intermediate and Conversion Thereof to a Triethylene Tetramine Derivative The procedure of Example 10 is repeated except that the following quantities of the following materials are used in the first stage reaction: 51.5 grams (0 25 mol) of 2,6-di-tert-butylphenol, 7.5 grams (0.25 mol) of paraformaldehyde, 110 grams (0 25 mol) of a polyoxyalkylene triamine having an average molecular weight of about 440 (Jeffamine T-403 amine; Texaco Chemical Company), and 300 grams of xylene. After collecting approximately 4 grams of water, the second stage is conducted in the same reaction vessel using 22.5 grams (0.25 mol) of dimethyl carbonate, and 36.5 grams (0.25 mol) of triethylene tetramine.

EXAMPLE 13-15

Preparation of Mannich Base Intermediates and Conversion Thereof to Triethylene Tetramine Derivatives The procedures of Examples 10-12 are repeated except that in each case the 2,6-di-tert-butylphenol is replaced by an amount 2,4-di-tert-butylphenol equivalent to the amount of 2,6-di-tert-butylphenol used in the respective Examples.

EXAMPLES 16-18

Preparation of Mannich Base Intermediates and Conversion Thereof to Triethylene Tetramine Derivatives The procedures of Examples 10-12 are repeated except that the 2,6-di-tert-butylphenol is replaced, respectively, by 0.4, 0.25 and 0.25 mol of 2-methyl-6-tert-butylphenol.

EXAMPLE 19-21

Preparation of Mannich Base Intermediates and Conversion Thereof to Triethylene Tetramine Derivatives The procedures of Examples 10-12 are repeated except that the 2,6-di-tert-butylphenol is replaced, respectively, by 0.4, 0.25 and 0.25 mol of 2,6-diisopropylphenol.

EXAMPLES 22-24

Preparation of Mannich Base Intermediates and Conversion Thereof to Triethylene Tetramine Derivatives The procedures of Examples 10-12 are repeated except that the 2,6-di-tert-butylphenol is replaced, respectively, by 0.4, 0.25 and 0.25 mol of p-nonylphenol formed by alkylating phenol with propylene trimer.

EXAMPLES 25-27

Preparation of Mannich Base Intermediates and Conversion Thereof to Triethylene Tetramine Derivatives The procedures of Examples 10-12 are repeated except that the 2,6-di-tert-butylphenol is replaced, respectively, by 0.4, 0.25 and 0.25 mol of a mixture of p-alkylphenols having a VPO molecular weight of approximately 910 formed by alkylating phenol with a propylene oligomer mixture having approximately 60 carbon atoms.

The effectiveness of the compounds of this invention as detergent/dispersants for fuels and lubricants was demonstrated by comparative engine tests. These tests involved use of a standard engine test procedure for determining the amount of intake valve deposits formed when operating the engine for a test period of 150 hours on the test fuel. The base fuel used in these tests was an additive-free gasoline (Phillips J-42). Each test started with a clean intake valve and upon completion of the 150-hour test, the weight of the intake valve deposits was determined. Therefore the lower the weight of deposits, the more effective the composition.

Two different additives of this invention were subjected to the foregoing test. Thus "Invention Fuel A" was composed of the base fuel containing 100 pounds per thousand barrels of a compound of this invention formed as in Example 2. "Invention Fuel B" was composed of the base fuel containing 100 pounds per thousand barrels of a compound of this invention formed as in Example 3.

The results of these tests are summarized in Table IV.

TABLE IV

| Fuel Composition | Weight of Intake Valve Deposits |
|---|---|
| Additive-free base fuel | 370 mg |
| Invention Fuel A | 43 mg |
| Invention Fuel B | 3.3 mg |

Generally speaking, the fuels of this invention will contain up to about 2% by weight of a compound of this invention. The fuels can be any middle distillate fuel such as gasoline (including so-called reformulated gasolines which contain oxygenates such as alcohols and/or ethers), diesel fuels, kerosenes, jet fuels, burner fuels, home heating oils, gas oils, and the like.

As noted above, the compounds of this invention are also effective as dispersants for use in natural and synthetic oils of lubricating viscosity. Amounts in the range of from about 0.5 to about 5% based on the weight of the finished lubricant or functional fluid composition are generally sufficient to provide effective dispersancy. The compounds of this invention exhibit good compatibility with conventional lubricant additives such as metal-containing detergents, antiwear agents, extreme pressure agents, corrosion inhibitors, foam inhibitors, friction modifiers, viscosity index improvers, pour point depressants, oxidation inhibitors, and the like.

This invention is susceptible to considerable variation in its practice. Accordingly, this invention is not intended to be limited by the specific exemplifications set forth hereinabove. Rather, this invention is intended to cover the subject matter within the spirit and scope of the appended claims and the permissible equivalents thereof.

I claim:

1. A compound in which a phenolic moiety is linked by a Mannich base linkage to an alkylene-poly(oxyalkylene) moiety, and a polyamine moiety is linked to the alkylene-poly(oxyalkylene) moiety by a urea linkage involving one of the nitrogen atoms of the polyamine moiety.

2. A compound in accordance with claim 1 having the formula:

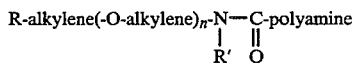

where R is a hydroxybenzylamino group, the alkylene groups can be the same or different and contain from 2 to about 20 carbon atoms each, n is a number in the range of from 2 to 150, R' is a hydrogen atom or a hydrocarbyl group, and the polyamine group has 2 to 10 nitrogen atoms, and is bonded to the carbonyl group by means of one of said nitrogen atoms thereof.

3. A compound in accordance with claim 2 wherein the alkylene groups of said compound contain 2 to 10 carbon atoms each, R' is a hydrogen atom, and the polyamine group of said compound has at least one primary amino group.

4. A compound in accordance with claim 2 wherein the hydroxybenzylamino group of said compound has from 1 to 2 acyclic hydrocarbyl substituents on the ring thereof, the alkylene groups of said compound contain 2 to 5 carbon atoms each, n is in the range of about 5 to about 90, R' is a hydrogen atom, and the polyamine group of said compound has at least one primary amino group.

5. A compound in accordance with claim 2 wherein the hydroxybenzylamino group of said compound has an acyclic hydrocarbyl substituent in the para-position on the ring thereof, the alkylene groups of said compound contain from 3 to 4 carbon atoms each, R' is a hydrogen atom, n is in the range of about 10 to about 80, and the polyamine group of said compound has at least one primary amino group.

6. A compound in accordance with claim 1 having the formula:

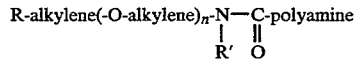

where R is a 3,5-dihydrocarbyl-4-hydroxybenzylamino group or a 3,5-dihydrocarbyl-2-hydroxybenzylamino group, the alkylene groups can be the same or different and contain from 2 to 20 carbon atoms each, n is a number in the range of 2 to 150, R' is a hydrogen atom or a hydrocarbyl group, and the polyamine group has 2 to 10 nitrogen atoms, and is bonded to the carbonyl group by means of one of said nitrogen atoms thereof.

7. A compound in accordance with claim 6 wherein the alkylene groups of said compound contain 2 to 10 carbon atoms each, R' is a hydrogen atom, and the polyamine group of said compound has at least one primary amino group.

8. A compound in accordance with claim 6 wherein the hydroxybenzylamino group of said compound is a 3,5-dialkyl-4-hydroxybenzylamino group or a 3,5-dialkyl-2-hydroxybenzylamino group, the alkylene groups of said compound contain 2 to 5 carbon atoms each, n is in the range of about 5 to about 90, R' is a hydrogen atom, and the polyamine group of said compound has at least one primary amino group.

9. A compound in accordance with claim 6 wherein the hydroxybenzylamino group of said compound is a 3,5-dialkyl-4-hydroxybenzylamino group in which at least one of said alkyl groups is a tertiary alkyl group or a 3,5-dialkyl-2-hydroxybenzylamino group in which at least one of said alkyl groups is a tertiary alkyl group, the alkylene groups of said compound contain from 3 to 4 carbon atoms each, R' is a hydrogen atom, n is in the range of about 10 to about 80, and the polyamine group of said compound has at least one primary amino group.

10. A compound in accordance with claim 1 having the formula:

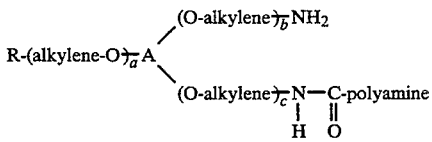

where R is a hydroxybenzylamino group, the alkylene groups can be the same or different and contain from 2 to about 20 carbon atoms each, A is the hydrocarbyl group of a triol, and a, b and c are numbers in the range of 1 to about 35 with the total of a, b and c being in the range of about 5 to about 100, and the polyamine group has 2 to 10 nitrogen atoms, and is bonded to the carbonyl group by means of one of said nitrogen atoms thereof.

11. A compound in accordance with claim 10 wherein the alkylene groups of said compound contain 2 to 10 carbon atoms each, and the polyamine group of said compound has at least one primary amino group.

12. A compound in accordance with claim 10 wherein the hydroxybenzylamino group of said compound has from 1 to 2 acyclic hydrocarbyl substituents on the ring thereof, the alkylene groups of said compound contain 2 to 5 carbon atoms each, and the polyamine group of said compound has at least one primary amino group.

13. A compound in accordance with claim 10 wherein the hydroxybenzylamino group of said compound has an acyclic hydrocarbyl substituent in the para-position on the ring thereof, the alkylene groups of said compound contain from 3 to 4 carbon atoms each, and the polyamine group of said compound has at least one primary amino group.

14. A compound in accordance with claim 10 wherein the hydroxybenzylamino group of said compound is a 3,5-dihydrocarbyl-4-hydroxybenzylamino group or a 3,5-dihydrocarbyl-2-hydroxybenzylamino group, the alkylene groups of said compound contain 2 to 5 carbon atoms each, and the polyamine group of said compound has at least one primary amino group.

15. A compound in accordance with claim 10 wherein the hydroxybenzylamino group of said compound is a 3,5-dialkyl-4-hydroxybenzylamino group in which at least one of said alkyl groups is a tertiary alkyl group or a 3,5-dialkyl-2-hydroxybenzylamino group in which at least one of said alkyl groups is a tertiary alkyl group, the alkylene groups of said compound contain from 3 to 4 carbon atoms each, and the polyamine group of said compound has at least one primary amino group.

16. A compound in accordance with claim 1 having the formula:

$$R\text{-(alkylene-O)}_a\text{-}A\begin{array}{c}(\text{O-alkylene})_b\text{-}\underset{H}{N}\text{-}\underset{O}{\overset{\|}{C}}\text{-polyamine}\\(\text{O-alkylene})_c\text{-}\underset{H}{N}\text{-}\underset{O}{\overset{\|}{C}}\text{-polyamine}\end{array}$$

where R is a hydroxybenzylamino group, the alkylene groups can be the same or different and contain from 2 to about 20 carbon atoms each, A is the hydrocarbyl group of a triol, and a, b and c are numbers in the range of 1 to about 35 with the total of a, b and c being in the range of about 5 to about 100, and each polyamine group has 2 to 10 nitrogen atoms, and is bonded to the carbonyl group by means of one of said nitrogen atoms thereof.

17. A compound in accordance with claim 16 wherein the alkylene groups of said compound contain 2 to 5 carbon atoms each, and each polyamine group of said compound has at least one primary amino group.

18. A compound in accordance with claim 1 wherein each alkylene group of said alkylene-poly(oxyalkylene) moiety contains 3 carbon atoms.

19. A compound in accordance with claim 1 wherein the polyamine moiety is derived from an alkylene polyamine.

20. A compound in accordance with claim 1 wherein the polyamine moiety is derived from diethylene triamine or triethylene tetramine.

21. A compound in accordance with claim 1 wherein each alkylene group of said alkylene-poly(oxyalkylene) moiety contains 3 carbon atoms and wherein the polyamine moiety is derived from a mixture of straight chain, branched chain and cyclic ethylene polyamines having about 2 to about 10 nitrogen atoms in the molecule.

22. A compound in accordance with claim 1 wherein the phenolic moiety is derived from a 2,6-dihydrocarbyl phenol, a 2,4-dihydrocarbyl phenol or a 4-hydrocarbyl phenol, each alkylene group of said alkylene-poly(oxyalkylene) moiety contains 3 to 4 carbon atoms and wherein the polyamine moiety is derived from a mixture of straight chain, branched chain and cyclic ethylene polyamines having about 2 to about 10 nitrogen atoms in the molecule.

23. A compound in accordance with claim 22 wherein the phenolic moiety is derived from a 2,6-dialkyl phenol or a 2,4-dialkyl phenol and wherein at least one of the alkyl groups of said 2,6- or 2,4-dialkyl phenol is a tertiary alkyl group.

24. A compound in accordance with claim 22 wherein the phenolic moiety is derived from a 4-hydrocarbyl phenol in which the hydrocarbyl group is derived from a propylene oligomer and contains in the range of about 9 to about 90 carbon atoms.

25. A process for the preparation of a compound according to claim 1 which comprises:
   a) reacting a phenolic compound with an aldehyde and a compound of the formula:

$$H_2N\text{-alkylene}(\text{-O-alkylene})_n\text{-}NH_2$$

wherein the alkylene groups can be the same or different and contain from 2 to 20 carbon atoms each, and n is a number in the range of 2 to 150, to form a Mannich base; and
   b) reacting said Mannich base with a dialkylcarbonate or phosgene and a polyamine having 2 to 10 nitrogen atoms per molecule.

26. A process according to claim 25 wherein the phenolic compound is a 2,6-dihydrocarbylphenol, a 2,4-dihydrocarbylphenol or a 4-hydrocarbylphenol, wherein the aldehyde is formaldehyde or a formaldehyde-forming reagent, wherein said alkylene groups each contain 3 to 4 carbon atoms and wherein n is in the range of 2 to 100.

27. A process for the preparation of a compound according to claim 1 which comprises:
   a) reacting a phenolic compound with an aldehyde and a compound of the formula:

$$A\begin{array}{c}(\text{O-alkylene})_a\\(\text{O-alkylene})_b\\(\text{O-alkylene})_c\end{array}$$

wherein the alkylene groups can be the same or different and contain from 2 to 20 carbon atoms each, A is the hydrocarbyl group of a triol, and a, b and c are numbers in the range of 1 to about 35 with the total of a, b and c being in the range of about 5 to about 100, to form a Mannich base; and
   b) reacting said Mannich base with a dialkylcarbonate or phosgene and a polyamine having 2 to 10 nitrogen atoms per molecule.

28. A process according to claim 27 wherein the phenolic compound is a 2,6-dihydrocarbylphenol, a 2,4-dihydrocarbylphenol or a 4-hydrocarbylphenol, wherein the aldehyde is formaldehyde or a formaldehyde-forming reagent, and wherein said alkylene groups each contain 3 to 4 carbon atoms.

29. A distillate fuel for use in an internal combustion engine containing a compound according to claim 1 in an amount at least sufficient to control induction system deposit formation.

30. A method of inhibiting the formation of induction system deposits in an internal combustion engine burning a distillate fuel, which method comprises operating said engine with a distillate fuel composition containing a compound according to claim 1 in an amount at least sufficient to control induction system deposit formation.

* * * * *